(12) United States Patent
Wochner et al.

(10) Patent No.: US 10,605,659 B2
(45) Date of Patent: Mar. 31, 2020

(54) PROCESS FOR DETERMINING SURFACE CONTAMINATION OF POLYCRYSTALLINE SILICON

(71) Applicants: Hanns Wochner, Burghausen (DE); Robert Baumann, Burghausen (DE)

(72) Inventors: Hanns Wochner, Burghausen (DE); Robert Baumann, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 1115 days.

(21) Appl. No.: 13/738,973

(22) Filed: Jan. 10, 2013

(65) Prior Publication Data
US 2013/0186325 A1 Jul. 25, 2013

(30) Foreign Application Priority Data
Jan. 24, 2012 (DE) .................. 10 2012 200 994

(51) Int. Cl.
| | |
|---|---|
| G01J 3/28 | (2006.01) |
| C01B 33/02 | (2006.01) |
| C01B 33/021 | (2006.01) |
| C01B 33/035 | (2006.01) |
| C23C 16/24 | (2006.01) |
| C30B 13/00 | (2006.01) |
| G01N 21/64 | (2006.01) |

(52) U.S. Cl.
CPC .............. G01J 3/28 (2013.01); C01B 33/02 (2013.01); C01B 33/021 (2013.01); C01B 33/035 (2013.01); C23C 16/24 (2013.01); C30B 13/00 (2013.01); G01N 21/6489 (2013.01)

(58) Field of Classification Search
CPC ............. C30B 13/00; A61M 2025/024; A61M 2025/0253; A61M 2025/026; A61M 2025/028; A61M 25/02; C01B 33/02; C01B 33/021; C01B 33/035; C23C 16/24; G01J 3/28; G01N 21/6489
See application file for complete search history.

(56) References Cited

U.S. PATENT DOCUMENTS

| | | | |
|---|---|---|---|
| 4,921,026 A | | 5/1990 | Flagella et al. |
| 5,361,128 A | * | 11/1994 | Bourbina ................. C30B 13/00 356/311 |
| 5,436,164 A | * | 7/1995 | Dumler ................... G01N 33/20 117/38 |
| 6,309,467 B1 | | 10/2001 | Wochner et al. |
| 2006/0000409 A1 | * | 1/2006 | Spangler .................. C30B 28/06 117/81 |
| 2009/0311161 A1 | * | 12/2009 | Mozer .................... C01B 33/037 423/348 |
| 2010/0001106 A1 | | 1/2010 | Schaefer et al. |
| 2010/0154357 A1 | * | 6/2010 | Wochner ................. B65B 25/00 53/405 |
| 2011/0083249 A1 | | 4/2011 | Wochner |

FOREIGN PATENT DOCUMENTS

| | | |
|---|---|---|
| DE | 3007377 A1 | 9/1981 |
| DE | 4137521 A1 | 5/1992 |
| DE | 4330598 A1 | 4/1994 |
| DE | 102006035081 A1 | 1/2008 |
| DE | 102008040231 A1 | 12/2008 |
| EP | 0345618 A2 | 12/1989 |
| EP | 0905796 B1 | 4/2002 |

OTHER PUBLICATIONS

Measurement of Carbon Concentration in Polycrystalline Silicon Using FTIR, Lydia L. Hwang, John Bucci, and James R. McCormick, J. Electrochem. Soc., vol. 138, No. 2, Feb. 1991, 576-581.*
Hwang et al "Measurement of Carbon Concentration in Polycrystalline Silicon Using FTIR", J. Electrochem. Soc., vol. 138, No. 2, 576-581, Feb. 1991.*
Hwang et al, "Measurement of Carbon Concentration in Polycrystalline Silicon Using FTIR", J. Electrochem. Soc., vol. 138, No. 2, Feb. 1991, pp. 576-581.*
Abstract in English for DE 3007377 A1.
PatBase abstract for DE 10 2008 040 231.

* cited by examiner

*Primary Examiner* — Hua Qi
(74) *Attorney, Agent, or Firm* — Caesar Rivise, PC

(57) ABSTRACT

The invention provides a process for determining surface contamination of polycrystalline silicon, including the steps of: a) providing two polycrystalline silicon rods by deposition in a Siemens reactor; b) determining contaminants in the first of the two rods immediately after the deposition; c) conducting the second rod through one or more systems in which polycrystalline silicon rods are processed further to give rod pieces or polysilicon fragments, optionally cleaned, stored or packed; d) then determining contaminants in the second rod; wherein the difference in the contaminants determined in the first and second rods gives surface contamination of polycrystalline silicon resulting from systems and the system environment.

15 Claims, No Drawings

PROCESS FOR DETERMINING SURFACE CONTAMINATION OF POLYCRYSTALLINE SILICON

BACKGROUND OF THE INVENTION

The invention provides a process for determining surface contamination of polycrystalline silicon.

On the industrial scale, crude silicon is obtained by the reduction of silicon dioxide with carbon in a light arc furnace at temperatures of about 2000° C.

This affords "metallurgical grade" silicon ($Si_{mg}$) having a purity of about 98-99%.

For applications in photovoltaics and in microelectronics, the metallurgical grade silicon has to be purified.

For this purpose, it is reacted, for example, with gaseous hydrogen chloride at 300-350° C. in a fluidized bed reactor to give a silicon-containing gas, for example trichlorosilane. This is followed by distillation steps in order to purify the silicon-containing gas.

This high-purity silicon-containing gas then serves as a starting material for the production of high-purity polycrystalline silicon.

The polycrystalline silicon, often also called polysilicon for short, is typically produced by means of the Siemens process. This involves heating thin filament rods of silicon by direct passage of current in a bell-shaped reactor ("Siemens reactor"), with introduction of a reaction gas comprising a silicon-containing component and hydrogen.

The silicon-containing component of the reaction gas is generally monosilane or a halosilane of the general composition $SiH_nX_{4-n}$ (n=0, 1, 2, 3; X=Cl, Br, I). It is preferably a chlorosilane, more preferably trichlorosilane. Predominantly $SiH_4$ or $SiHCl_3$ (trichlorosilane, TCS) is used in a mixture with hydrogen.

In the Siemens process, the filament rods are typically inserted perpendicularly into electrodes present at the reactor base, through which they are connected to the power supply. Every two filament rods are coupled via a horizontal bridge (likewise composed of silicon) and form a support body for the silicon deposition. The bridge coupling produces the typical U shape of the support bodies, which are also called thin rods.

High-purity polysilicon is deposited on the heated rods and the bridge, as a result of which the rod diameter grows with time (CVD=Chemical Vapor Deposition/gas phase deposition).

After the deposition has ended, these polysilicon rods are typically processed further by means of mechanical processing to give fragments of different size classes, optionally subjected to a wet-chemical purification and finally packed.

The polysilicon can, however, also be processed further in the form of rods or rod pieces. This is especially true for the use of the polysilicon in an FZ process.

In addition, another known method is to expose small silicon particles directly to such a reaction gas in a fluidized bed reactor. The polycrystalline silicon produced is in the form of granules (granular poly).

Polycrystalline silicon (polysilicon for short) serves as a starting material in the production of monocrystalline silicon by means of crucible pulling (Czochralski or CZ process) or by means of zone melting (float zone or FZ process). This monocrystalline silicon is divided into wafers and, after a multitude of mechanical, chemical and chemomechanical processing operations, used in the semiconductor industry for manufacture of electronic components (chips).

More particularly, however, polycrystalline silicon is increasingly being required for production of mono- or multicrystalline silicon by means of pulling or casting processes, this mono- or multicrystalline silicon serving for production of solar cells for photovoltaics.

Since the quality demands on polysilicon are becoming ever higher, quality control over the entire process chain is indispensible. The material is analyzed, for example, with regard to contaminations with metals or dopants. Contamination in bulk should be distinguished from contamination at the surface of the polysilicon fragments or rod pieces.

It is customary to convert the polysilicon produced to monocrystalline material for the purposes of quality control. In this case, the monocrystalline material is analyzed. Here too, metal contaminations, which are assessed particularly critically in the customer processes in the semiconductor industry, are of particular significance. The silicon is, however, also analyzed with regard to carbon and dopants such as aluminum, boron, phosphorus and arsenic.

Dopants (B, P, As, Al) are analyzed by means of photoluminescence to SEMI MF 1398 on an FZ single crystal produced from the polycrystalline material (SEMI MF 1723).

As an alternative, low-temperature FTIR (Fourier Transform IR spectroscopy) is used (SEMI MF 1630).

The fundamentals of the FZ process are described, for example, in DE-3007377 A.

In the FZ process, a polycrystalline stock rod is gradually melted with the aid of a high-frequency coil, and the molten material is converted to a single crystal by seeding with a monocrystalline seed crystal and subsequent recrystallization. In the course of recrystallization, the diameter of the single crystal forming is first increased in a cone shape (cone formation) until a desired final diameter has been attained (rod formation). In the cone formation phase, the single crystal is also mechanically supported in order to take the load off the thin seed crystal.

A wafer is cut off the monocrystalline rod produced by means of FZ from a polycrystalline silicon rod (SEMI MF 1723). A small wafer is cut out of the pulled mono-crystalline rod, etched with HF/HNO3, rinsed with 18 MOHm water and dried. The photoluminescence measurements are conducted on this wafer.

FTIR (SEMI MF 1188, SEMI MF 1391) enables the determination of carbon and oxygen concentrations.

This involves cutting a small wafer out of a poly-crystalline rod. The wafer is polished. Subsequently, the carbon content is determined by means of FTIR spectroscopy.

Both processes (photoluminescence and FTIR) serve exclusively for determination of contaminants in bulk.

Contaminants at the surface can be determined only indirectly.

DE 41 37 521 A1 describes a process for analyzing the concentration of contaminants in silicon particles, which comprises adding particulate silicon to a silicon vessel, processing the particulate silicon and the silicon vessel to give monocrystalline silicon in a float zone, and determining the concentration of contaminants present in the monocrystalline silicon. The concentrations of boron, phosphorus, aluminum and carbon in the silicon vessel used were determined and give a reproducible background value.

The values for boron, phosphorus and carbon found by means of FTIR by the float zone process were corrected by the proportion which originated from the silicon vessel.

In this application, it is also shown that the fragmentation of a polycrystalline silicon rod leads to contamination of the silicon. This is possible by virtue of silicon fragments being introduced into the silicon vessel, subjected to the float zone process and then analyzed for contaminants by means of FTIR. Since the contamination of the base material prior to fragmentation is known, the additional contamination resulting from the fragmentation can be concluded.

DE 43 30 598 A1 likewise discloses a process which enables the contamination of silicon resulting from comminution processes to be concluded. A silicon block was broken into lumps. The silicon lump was subsequently subjected to a zone melting process and converted to a single crystal. A wafer was sawn out of the single crystal and analyzed for boron and phosphorus by means of photoluminescence. Compared to the average boron and phosphorus contents of the silicon block used, an increase in the boron and phosphorus concentrations is found, which is attributable to factors including the comminution process.

The processes described, however, do not take into account the fact that the environment in which not only the comminution process but also other process steps such as storage, transport, cleaning and packaging take place also has an influence on the contamination of the silicon, especially on the surface contamination thereof.

A purely analytical process for test purposes is inadequate in this regard.

The problems described gave rise to the objective of the invention.

DESCRIPTION OF THE INVENTION

This object is achieved by a process for determining surface contamination of polycrystalline silicon, comprising the steps of
a) providing two polycrystalline silicon rods by deposition in a Siemens reactor;
b) determining contaminants in the first of the two rods immediately after the deposition;
c) conducting the second rod through one or more systems in which polycrystalline silicon rods are processed further to give rod pieces or polysilicon fragments, optionally cleaned, stored or packed;
d) then determining contaminants in the second rod;
wherein the difference in the contaminants determined in the first and second rods gives surface contamination of polycrystalline silicon resulting from systems and the system environment.

First of all, two polycrystalline silicon rods are provided, by depositing polycrystalline silicon in a Siemens reactor, giving rise to U-shaped polycrystalline silicon bodies each comprising two polycrystalline silicon rods.

The reaction gas used in the deposition typically comprises a silicon-containing component, preferably trichlorosilane, and hydrogen.

The deposition is preferably effected in a small test reactor.

In practice, an aforementioned U-shaped body, after the deposition, can be deinstalled from the reactor, and then the bridge and respective rod ends are removed, so as to obtain two polycrystalline silicon rods from one and the same batch.

The two polycrystalline silicon rods provided in step a) were preferably joined to one another (brother rods) via a bridge (U shape) during the deposition.

In the case of use of a small reactor, the two polycrystalline silicon rods may typically have a length of about 20 cm and a diameter of about 1.6 cm.

One of the two rods is preferably packed in a PE bag immediately after the deposition and the separation of bridge and rod end. The two rods are preferably each packed in a PE bag.

This first rod is subsequently analyzed for contamination.

Preference is given to determining dopants and carbon.

In an analytical laboratory to which the packed rod is transported, preference is given to removing the rod from the PE bag, separating a wafer from the poly-crystalline rod and sending it to the FTIR analysis.

This determines the carbon concentration.

The remaining rod is preferably converted by means of FZ to a monocrystalline rod.

The concentration of dopants is determined therein by means of photoluminescence.

The values thus determined for dopant and carbon concentrations serve as reference values for the second rod.

The second rod, after removal from the PE bag, is preferably conducted through the systems for the production of polycrystalline silicon chunks (comminution, packaging) and optionally through the systems for cleaning of polycrystalline silicon chunks).

In the course of this, the rod takes up the contaminants in terms of dopants and carbon while passing through the systems.

After passing through the cleaning systems or the production line for uncleaned chunk poly, the contaminated rod is preferably packed again in a high-purity PE bag.

Preferably two labels are stuck onto the PE bag:
Label No. 1: Label with the batch number of the original batch (comparison with first rod)
Label No. 2: Label with a new batch number The contaminated rod is used to produce a monocrystalline rod by means of FZ.

Subsequently—as described above for the first rod—dopants are determined by means of photoluminescence, and carbon by means of FTIR.

In contrast to the first rod, the determination of the carbon concentration by means of FTIR is effected not on a polycrystalline wafer but on a monocrystalline wafer.

In the course of FZ pulling of the contaminated rod, the carbon-containing particles migrate from the surface into the bulk and thus become amenable to carbon measurement by means of FTIR.

The values measured for the first rod are subtracted from the values for the second rod conducted through the systems.

The differences between the first and second rods then give rise to the value which can be attributed to the surface of the polycrystalline silicon after processing, cleaning, packaging.

The process according to the invention thus makes it possible to determine indirectly how polysilicon is contaminated at the surface in the course of the processing steps such as comminution, cleaning, packaging, or in transport operations.

The process thus gives surface contaminations for all possible products, such as polysilicon rods, cut rods and polysilicon chunks of different size classes (etched or unetched).

The process also enables monitoring and optimization of individual production steps with regard to surface contamination:

For example, the second rod can be conducted only through the cleaning system or only through the comminution system. In that case, the process separately gives the influence of the comminution system and the environment thereof, or of the cleaning system and the environment thereof, on surface contamination. The same applies to the packing of poly-silicon or the transport of the polysilicon from one system to another system.

The determination of the surface contamination is reproducible.

For testing, twelve rods in twelve process dishes were run through the cleaning system at the same time.

Subsequently, the dopant concentrations were determined by means of photoluminescence.

Theoretically, the twelve brother rods, even though they originate from different batches, should have the same analysis values for boron, phosphorus, aluminum and arsenic, since they have been run through the cleaning system simultaneously under the same conditions.

Table 1 shows the values determined for boron, phosphorus, aluminum and arsenic in ppta.

The values measured for the first rod were subtracted from the values for the second rod conducted through the systems.

TABLE 1

|     | B     | P     | Al    | As    |
|-----|-------|-------|-------|-------|
| #1  | 20.95 | 23.37 | 0.98  | 4.95  |
| #2  | 12.74 | <1    | <0.5  | <0.5  |
| #3  | 14.40 | 1.25  | <0.5  | 2.04  |
| #4  | 16.04 | 5.49  | <0.5  | 0.52  |
| #5  | 20.96 | 10.09 | <0.5  | <0.5  |
| #6  | 17.79 | 7.22  | 0.52  | <0.5  |
| #7  | 12.28 | <1    | <0.5  | <0.5  |
| #8  | 14.03 | <1    | <0.5  | <0.5  |
| #9  | 22.15 | 13.85 | <0.5  | 1.60  |
| #10 | 21.98 | 7.51  | <0.5  | 2.03  |
| #11 | 12.49 | 1.52  | <0.5  | 1.71  |
| #12 | 22.91 | 14.86 | 0.50  | <0.5  |

The following reproducibilities and detection limits were estimated:

Boron
  Reproducibility: +/−5 ppta
  Detection limit: 5 ppta
Phosphorus
  Reproducibility: +/−5 ppta
  Detection limit: 5 ppta
Aluminum
  Reproducibility: +/−0.25 ppta
  Detection limit: 1 ppta
Arsenic
  Reproducibility: +/−0.5 ppta
  Detection limit: 5 ppta The process according to the invention can also be used to determine the content of carbon particles on the silicon surface with a reproducibility of +/−10 ppba at a detection limit of 10 ppba.

Example

The example shows how the second rod is conducted through the cleaning system and then analyzed for dopant concentration. The first rod (brother rod of the second rod from a U-shaped body after deposition) was analyzed as described above for dopants by means of photoluminescence.

The PE bag in which the second rod (length 20 cm, diameter 1.6 cm) has been packed is opened with scissors, preferably ceramic scissors. The rod is removed, using an ultraclean glove for manual removal. Subsequently, the rod is placed into a process dish.

A suitable ultraclean glove (PE-Tyvek® glove) is disclosed in US 2011-0083249, which is fully incorporated here by reference. Tyvek® from DuPont is a paper web-like fibrous functional textile composed of thermally welded fibers of high-density polyethylene (HDPE).

The process dish filled with the rod is run through the cleaning system.

In the course of this, the silicon rod, in a pre-purification, is washed with an oxidizing cleaning solution containing the compounds hydrofluoric acid (HF), hydrochloric acid (HCl) and hydrogen peroxide ($H_2O_2$). In a main cleaning operation, the rod is washed with a cleaning solution comprising nitric acid ($HNO_3$) and hydrofluoric acid (HF). Subsequently, the rod is washed with an oxidizing cleaning solution and thus hydrophilized. With regard to the cleaning process, EP 0 905 796 B1 is fully incorporated by reference.

After the rod has been cleaned, it is dried and, after cooling, grasped with an ultraclean glove, preferably a PE-Tyvek® glove, and packed in a high-purity PE bag which is sealed.

Two labels are stuck onto the PE bag:

Label No. 1: Label with the batch number of the original batch (enables comparison of the measurements with first rod)

Label No. 2: Label with a new batch number

The contaminated rod is processed by means of FZ to give a monocrystalline rod. As described above, dopants are determined by means of photoluminescence. It would likewise also be possible to analyze carbon by means of FTIR.

The values for the boron, phosphorus, aluminum and arsenic dopants measured for the first rod are subtracted from the corresponding values for the second rod.

The differences between the first and second rods then give the values which can be attributed to the surface of the polysilicon.

Table 2 shows the differences determined for surface contaminations of boron, phosphorus, aluminum and arsenic.

TABLE 2

| B      | P      | Al     | As    |
|--------|--------|--------|-------|
| 44.06  | 15.46  | 0.03   | 1.29  |
| 119.32 | 405.97 | 194.63 | 22.78 |
| 19.10  | 4.28   | 0.89   | 4.66  |
| 128.55 | 250.91 | 145.57 | 17.18 |
| 7.70   | 79.68  | 0.87   | 0.52  |
| 3.58   | 21.01  | 1.53   | 2.66  |
| 3.86   | 16.17  | 6.71   | 4.39  |
| 6.57   | 0.22   | 0.25   | 1.24  |
| 9.11   | 2.68   | 1.37   | 1.08  |
| 10.10  | 1.37   | 14.60  | 0.59  |
| 20.47  | 41.02  | 7.26   | 3.18  |

What is claimed is:

1. A process for determining surface contamination of polycrystalline silicon, comprising steps of
    a) providing two polycrystalline silicon rods by deposition in a Siemens reactor;
    b) determining a first concentration of non-carbon contaminants and a first concentration of carbon contaminants in a first rod of the two polycrystalline silicon rods after the deposition, wherein: i) a first rod wafer is removed from the first rod, ii) the first rod wafer is analyzed by FTIR to determine the first concentration of carbon contaminants, and iii) the first rod after removal of the first rod wafer is converted by a float zone process to a first monocrystalline rod, and the first concentration of non-carbon contaminants is determined by photoluminescence on a first monocrystalline rod wafer removed from the first monocrystalline rod;

c) conducting a second rod of the two polycrystalline silicon rods through at least one system for further processing polycrystalline silicon rods, wherein the further processing comprises comminution to provide rod pieces or polysilicon fragments, wherein the second rod is not comminuted and the first rod is not conducted through the at least one system;

d) determining contaminants in the second rod by processing the second rod by a float zone process to provide a second monocrystalline rod;

e) removing a FTIR wafer and a photoluminescence wafer from the second monocrystalline rod;

f) performing a FTIR analysis of the FTIR wafer to determine a second concentration of carbon contaminants;

g) performing a photoluminescence analysis of the photoluminescence wafer to determine a second concentration of non-carbon contaminants; and h) determining the surface contamination of polycrystalline silicon resulting from the at least one system and a system environment from a difference between the first concentration of the non-carbon contaminants and the second concentration of the non-carbon contaminants.

2. The process as claimed in claim 1, wherein the non-carbon contaminants of the first rod and the second rod are members selected from the group consisting of boron, phosphorus, aluminum and arsenic.

3. The process as claimed in claim 2, wherein the first rod is packed in a polyethylene bag after the deposition.

4. The process as claimed in claim 3, wherein in step c) the second rod is conducted through a comminution system and a packaging system.

5. The process as claimed in claim 3, wherein the further processing conducted by the at least one system in step c) comprises comminution, cleaning, storage and packaging of polysilicon, wherein the second rod is packed in a polyethylene bag but is not comminuted, cleaned or stored.

6. The process as claimed in claim 1, wherein the first rod is packed in a polyethylene bag after the deposition.

7. The process as claimed in claim 1, wherein the further processing conducted by the at least one system in step c) comprises comminution, cleaning, storage and packaging of polysilicon, wherein the second rod is packed in a polyethylene bag but is not comminuted, cleaned or stored.

8. The process as claimed in claim 1, wherein the second rod is cleaned, stored and packaged prior to step (d).

9. The process as claimed in claim 1, wherein the second rod is cleaned and packaged prior to step (d) but not stored.

10. The process as claimed in claim 1, wherein the second rod is cleaned and stored prior to step (d) but not packaged.

11. The process as claimed in claim 1, wherein the second rod is stored and packaged prior to step (d) but not cleaned.

12. The process as claimed in claim 1, wherein the second rod is packaged prior to step (d) but not cleaned or stored.

13. The process as claimed in claim 1, wherein the second rod is cleaned prior to step (d) but not stored or packaged.

14. The process as claimed in claim 1, wherein the second rod is stored prior to step (d) but not cleaned or packaged.

15. The process as claimed in claim 1, wherein the surface contamination in step (h) is determined from the difference between the first concentration of the non-carbon contaminants and the second concentration of the non-carbon contaminants and a difference between the first concentration of carbon contaminants and the second concentration of carbon contaminants.

* * * * *